US012127832B2

(12) United States Patent
Singh et al.

(10) Patent No.: US 12,127,832 B2
(45) Date of Patent: Oct. 29, 2024

(54) WEARABLE DEVICES WITH INTEGRATED CIRCUITRY

(71) Applicant: Bose Corporation, Framingham, MA (US)

(72) Inventors: Ankita Singh, Hudson, MA (US); Raymond O. England, East Greenwich, RI (US); Shawn Prevoir, Northborough, MA (US)

(73) Assignee: Bose Corporation, Framingham, MA (US)

( * ) Notice: Subject to any disclaimer, the term of this patent is extended or adjusted under 35 U.S.C. 154(b) by 556 days.

(21) Appl. No.: 16/176,859

(22) Filed: Oct. 31, 2018

(65) Prior Publication Data

US 2020/0129102 A1  Apr. 30, 2020

(51) Int. Cl.
*A61B 5/1455* (2006.01)
*A61B 5/00* (2006.01)
*A61B 5/024* (2006.01)

(52) U.S. Cl.
CPC ........ *A61B 5/14551* (2013.01); *A61B 5/0002* (2013.01); *A61B 5/02416* (2013.01); *A61B 5/486* (2013.01); *A61B 5/6802* (2013.01)

(58) Field of Classification Search
CPC .............. A61B 5/14551; A61B 5/0002; A61B 5/02416; A61B 5/486; A61B 5/6802
USPC .................................................... 340/539.12
See application file for complete search history.

(56) References Cited

U.S. PATENT DOCUMENTS

| 4,168,286 A * | 9/1979 | Moczygemba ........... C08F 8/04 |
| | | 525/289 |
| 2015/0155243 A1* | 6/2015 | Chen ....................... H01L 24/83 |
| | | 438/107 |
| 2015/0185178 A1* | 7/2015 | Lin ........................ C23C 18/165 |
| | | 204/403.01 |
| 2015/0359485 A1 | 12/2015 | Berg et al. |
| 2016/0339672 A1* | 11/2016 | Kagiyama ................. B32B 7/12 |
| 2017/0137611 A1* | 5/2017 | Kniess ..................... C08L 55/02 |
| 2018/0040722 A1* | 2/2018 | Obonai ............. H01L 21/02554 |

(Continued)

FOREIGN PATENT DOCUMENTS

WO    2016092472    6/2016
WO    2016145438    9/2016

OTHER PUBLICATIONS

Anonymus: "Molded interconnect device—Wikipedia, the free enclyclopedia", Feb. 9, 2015 (Feb. 9, 2015), XP055290225, Retrieved from the Internet: URL: https://en.wikipedia.org/w/index.php?title=Molded_interconnect_device&oldid=646412742 [retrieved on Jul. 21, 2016] the whole document.

(Continued)

*Primary Examiner* — Jack K Wang
(74) *Attorney, Agent, or Firm* — Bond, Schoeneck & King, PLLC

(57) ABSTRACT

A method of fabricating a wearable device having one or more integrated electronic components, including providing a substrate having an elastomeric material, at least one metal additive, and/or a carbon source additive; forming electrical circuitry within the elastomeric material by structuring one or more electrically conductive traces and plating the one or more electrically conductive traces; and providing the electrical circuitry with a sensor, wherein the sensor is configured to come in direct contact with skin of an individual.

20 Claims, 4 Drawing Sheets

(56) References Cited

U.S. PATENT DOCUMENTS

2018/0228063 A1* 8/2018 Dixon .................... H01L 23/36
2020/0084546 A1* 3/2020 Mainini ............... H04R 1/1016
2020/0123371 A1* 4/2020 Hara ........................ C08K 5/09

OTHER PUBLICATIONS

International Search Report and the Written Opinion of the International Searching Authority, International Application No. PCT/US2019/058784, pp. 1-14, dated Jan. 13, 2020.
Zhang et al., Selective Metallization Induced by Laser Activation: Fabricating Metallized Patterns on Polymer via Metal Oxide Composite, ACS Appl. Mater. Interfaces 2017, 9, 8996-9005, DOI: 10.1021/acsami.6b15828.

* cited by examiner

WEARABLE DEVICES WITH INTEGRATED CIRCUITRY

BACKGROUND

This disclosure generally relates to integrated circuit and sensor fabrication in wearable devices.

Wearable devices are being used for a growing variety of functions including fitness tracking, facilitating communication, synchronizing data, and monitoring health issues. The increasing commercialization of wearable devices is partly due to the miniaturization and integration of electronic components. Accordingly, wearable devices can incorporate electronic components (e.g., sensors, computer chips, and antennae) with lower profiles and smaller footprints in compact and aesthetically appealing designs. However, as consumers use wearable gadgets for longer periods of time, it is desirable to improve upon elements associated with comfort (e.g., stability, form-fitting aspects, and pressure exerted on the skin/body).

Accordingly, there is a need in the art for improved wearable devices having integrated electronic components and improved systems and methods for fabricating integrated antennae and circuit in compression, injection, thermoform and transfer molded soft articles for improved wearability.

SUMMARY

All examples and features mentioned below can be combined in any technically possible way.

In one aspect, a method of fabricating a wearable device having one or more integrated electronic components is provided. The method includes providing a substrate having an elastomeric material and at least one metal additive. Electrical circuitry is formed within the elastomeric material by structuring one or more electrically conductive traces and plating the one or more electrically conductive traces. Lastly, the electrical circuitry is provided with a sensor, wherein the sensor is configured to come in direct contact with skin of an individual.

Implementations may include one or more of the following. The step of providing the substrate can further include providing the substrate with a carbon source additive. The step of forming the electrical circuitry can involve activating one or more parts of the elastomeric material by laser etching to enable the plating of the one or more electrically conductive traces. The plating can be achieved by electroless or electrochemical plating. The sensor can be a biosensor configured to detect one or more health parameters and the biosensor can be coupled with the skin via dry electrode coupling. The method can further include providing the substrate overmolded on top of a rigid polymeric substrate. The step of providing the substrate can include providing the substrate with a foaming agent and the method can include extruding the substrate to form a foam. The method can further include coating a soft fabric with the substrate.

In another aspect, a wearable device includes a substrate having an elastomeric material and at least one metal additive. The wearable device also includes one or more electrically conductive traces structured and plated within the elastomeric material and a sensor configured to come in direct contact with skin of an individual.

Implementations may include one or more of the following. The at least one metal additive can include copper-chromium oxide. The substrate can further include a carbon source additive. The substrate can also include a foaming agent. The elastomeric material can include a durometer equal to or less than 80 Shore A. The sensor can be a biosensor configured to detect one or more health parameter and the biosensor can be coupled with the skin via dry electrode coupling. The wearable device can also include a support member, wherein the substrate is arranged on top of the support member. The one or more parts of the elastomeric material are activated by laser etching to enable the one or more electrically conductive traces to be plated. The one or more electrically conductive traces can be plated by electroless or electrochemical plating. The elastomeric material and the at least one metal additive can be mixed together at a predetermined ratio.

Implementations include an elastomeric substrate, a metal oxide additive and/or a carbon source additive depending on the type of elastomer used. Some elastomers, (e.g., natural rubber) contain carbon and thus would not need a carbon source additive. Other elastomers (e.g., silicone) do not contain carbon and thus would need a carbon source additive. In some implementations, carbon additives can activate metal oxides after the laser etching and plating process, the surface metal particles can facilitate fabricating integrated circuitry and sensors in compression, injection, thermoform and transfer molded soft articles.

Other features and advantages will be apparent from the description and the claims.

DETAILED DESCRIPTION

The present disclosure describes various soft wearable devices having integrated electronic components and systems and methods for fabricating integrated circuits, antennae and sensors in soft wearable devices. While electrical circuits are conventionally fabricated as printed circuit boards (PCBs) mounted within a housing of a product, various attempts have been made to reduce the time and components needed for such assembly processes. For example, PCB fabrication can be replaced by stereolithography-based 3D printing technologies to embed circuits on plastic housings. Another technology uses a laser direct structuring (LDS) process, which involves applying laser light to selectively activate desired surface regions of plastic carriers that are subsequently electroplated or electroless plated with metal to form patterned conductive structures. However, the plastic carriers are rigid thermoplastic polymers, for example, acrylonitrile-butadiene-styrene (ABS) doped with laser-activatable metal-polymer additives.

Applicant has recognized and appreciated that it would be beneficial to have integrated electronic components within wearable devices made of soft materials (e.g., rubbers), which are more comfortable to wear than hard plastics. Furthermore, in applications involving biosensors, Applicant has recognized and appreciated that providing sensors in soft conformable parts can enable better contact with the body to obtain better signal quality and improve on-body comfort. The term "rigid" as used herein should be construed to mean any material that is in its glassy state at room/use temperature. The term "soft" as used herein should be construed to mean any material that is in a rubbery plateau at room/use temperature.

Figure 1:
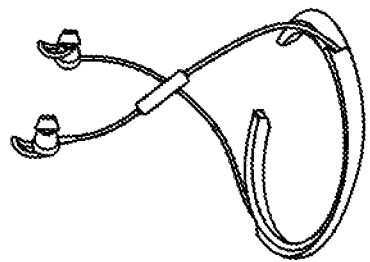
FIG. 1 shows a front perspective view of an example wearable device in isolation, in accordance with an embodiment.
Figure 2:
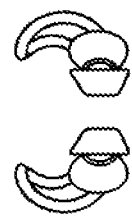
FIG. 2 shows a perspective view of another example wearable device in isolation, in accordance with an embodiment.
Figure 3:
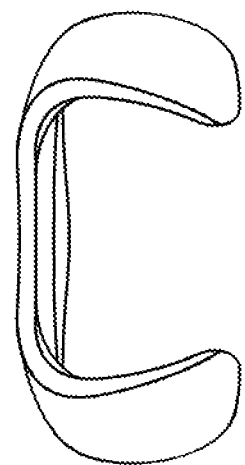
FIG. 3 shows a perspective view of another example wearable device in isolation, in accordance with an embodiment.
Figure 4:
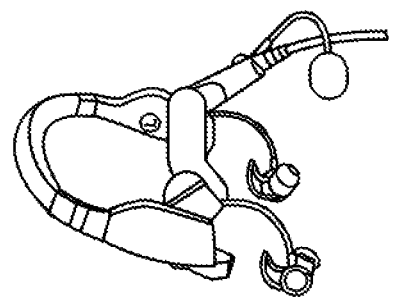
FIG. 4 shows a perspective view of another example wearable device in isolation, in accordance with an embodiment.

The examples and implementations disclosed or otherwise envisioned herein can be utilized with any suitable wearable device made of one or more elastomeric materials. Examples of suitable wearable devices include earbuds (e.g., Bose StayHear®+ tips manufactured by Bose Corporation of Framingham, Mass. in FIG. 1), headphones, (e.g., Bose QuietControl® 30 wireless headphones manufactured by Bose Corporation of Framingham, Mass. in FIG. 2), aviation headsets (e.g., Bose ProFlight aviation headset manufactured by Bose Corporation of Framingham, Mass. in FIG. 3), noise-blocking earplugs, hearing aids, augmented reality glasses, headbands, neckbands (e.g., Bose Soundwear Companion speaker manufactured by Bose Corporation of Framingham, Mass. in FIG. 4), wristwatches, and any other device to be worn in direct contact with the skin. However, the disclosure is not limited to these enumerated devices, and thus the disclosure described herein can encompass any wearable device.

Figure 5:
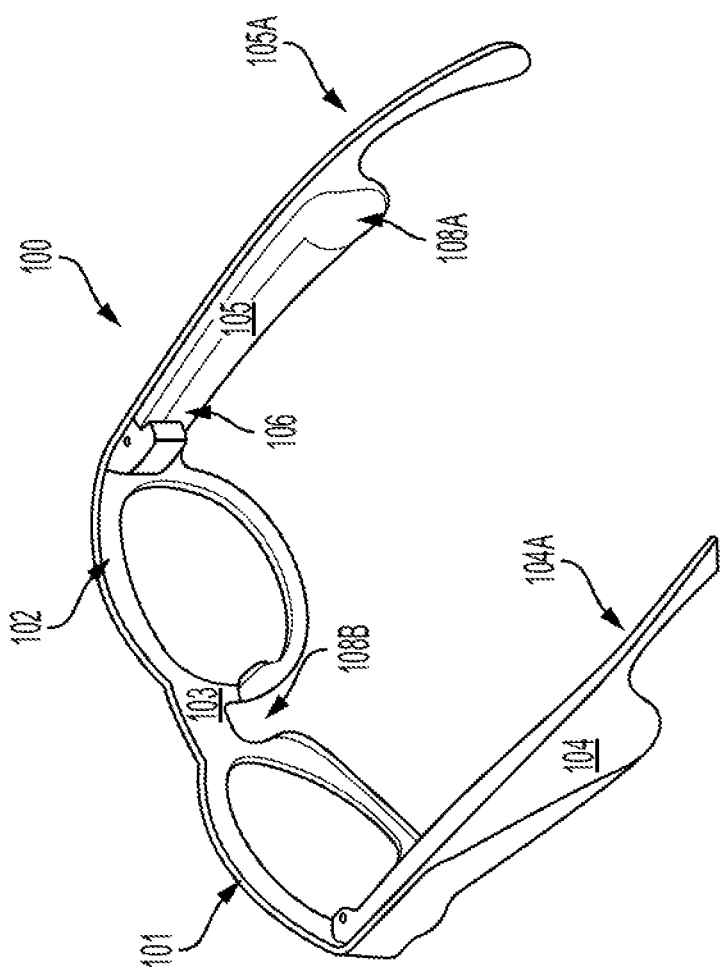
FIG. 5 is a rear perspective view of an example wearable device in isolation, in accordance with an embodiment.

Referring to FIG. 5, an example wearable device 100 is shown. Wearable device 100 includes eye frames 101 and 102, which are connected to each other by bridge 103. Eye frames 101 and 102 are also connected to temple arms 104 and 105, respectively, by any suitable mechanism, for example, hinges. In examples, wearable device 100 includes one or more embedded electrode sensors 108A and/or 108B and wearable device 100 can be operably coupled with an individual via one or more electrode sensors 108A and/or 108B. For example, embedded electrode sensors 108A and/or 108B can include one or more physiological electrodes for detecting one or more health parameters of an individual, including but not limited to electrocardiography (ECG), electromyogram (EMG), pulse rate, respiration rate, body temperature, sweat levels, glucose, electrooculogram (EOG), and electroencephalogram (EEG).

Figure 6:
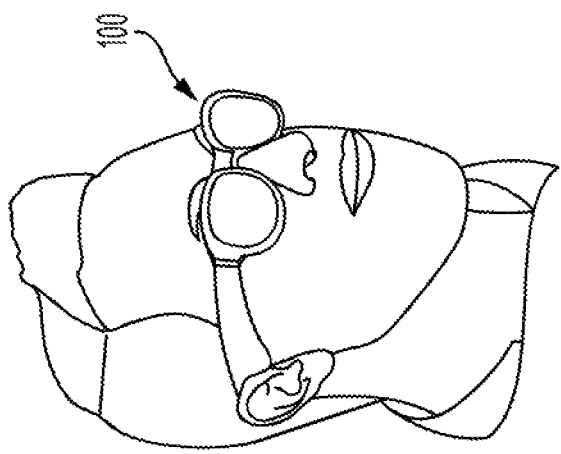
FIG. 6 shows a front perspective view of the example wearable device of FIG. 5 worn by a user, in accordance with an embodiment.

In examples, one or more physiological electrode sensors 108A and/or 108B are coupled with an individual via dry electrode coupling (e.g., direct contact between electrode and skin). Each physiological electrode 108A and 108B is configured to receive data from the body of the individual. The physiological electrodes make use of the natural pressure provided by wearable device 100 to hold the sensors securely in place at positions on the body. Physiological electrode 108A is positioned in temple arm 105 adjacent to temple tip 105A to contact the temple of an individual (as shown in FIG. 6). Although only a single electrode 108A is visible in FIG. 5, example wearable devices include two physiological electrodes, one for each temple. Thus, it should be appreciated that the inside surface of temple arm 104 adjacent to temple tip 104A can also include an embedded physiological electrode (despite not being visible in FIG. 5).

Physiological electrode 108B, which is also shown in FIG. 5, is positioned to contact the glabella (i.e., the portion of the body between the eyebrows). Although wearable device 100 in FIG. 5 includes sensors on the temples and the glabella, other example wearable devices can include additional or alternative sensors in different positions. For example, wearable devices can include sensors positioned farther back on temple tips 104A and 105A to contact skin located behind the ears. Example wearable devices can include a cEEG sensor grid directly plated on a soft part which enables better contact with the body and will also be comfortable. Other example wearable devices can include in-ear components and sensors positioned to contact skin within the ear.

In FIG. 5, each of electrode sensors 108A and 108B includes a first surface to contact the skin and a second surface opposite from the first surface connected to other components for amplifying, filtering, processing, recording, and/or transmitting acquired signals. The first surface of each of electrode sensors 108A and 108B can include a plurality or a pattern of protrusions to facilitate contact with the skin. Electrodes 108A and 108B and their electrical connections are integrated within wearable device 100.

In other examples, wearable device 100 further includes embedded integrated circuit 106, for example, inside the temple arms 104 or 105 proximate to one of the hinges. In examples, wearable device 100 is communicably coupled with an integrated circuit that is separate and remotely located, for example, in a computer or a mobile device. The integrated circuit can include a data processor, a memory, and a communication processor. Commands to be executed by the processor can be obtained via the communication processor. The communication processor facilitates wired or wireless communication for wearable device 100 and can be facilitated via one or more antennas, for example. The one or more antennas can be fabricated via the methods described herein. The communication processor can facilitate communication with one or more networks or other devices, for example, by using wireless methods that are known, including but not limited to Wi-Fi, Bluetooth, 3G, 4G, LTE, and/or ZigBee, among others. Wearable device 100 can further include an embedded power source (e.g., a battery) required to carry out various functionalities involving the integrated circuit and the one or more sensors described herein.

Wearable device 100 can be made of any suitable materials for stability, on-body comfort, and conformability. In examples, wearable device 100 is made of a silicone-based elastomeric polymer. In other examples, wearable device 100 can be made of fluoroelastomers (FKM), polyurethanes, thermosetting rubbers, compounded polynorbornene (e.g., Norsorex® material available from D-NOV GmbH of Vienna, Austria, product number M040822-15), shape memory polymers, or any other suitable materials. In examples, the material is characterized by a durometer equal to or less than 80 Shore A. In other examples, wearable device 100 includes a suitable soft (i.e., rubbery or conformable) elastomeric material on top of a rigid (i.e., glassy or nonconformable) support member for stability and longevity. For example, electrode sensors 108A and 108B in temple tip 105A and bridge 103, respectively, can be potted in a soft coating on top of a hard plastic. In alternate examples, wearable device 100 can be made of any suitable foam or flexible fabric.

The methods described herein focus on mixing suitable compounded rubber materials (e.g., liquid silicone rubber (LSR), high-consistency rubber (HCR), natural rubber, fluoroelastomers) with laser direct structuring (LDS) metal additives for fabricating small and inconspicuous on-part metal patterns (e.g., on the surfaces of wearable device 100). LDS metal additives include oxides of copper, nickel, gold, titanium, and silver, etc.

Figure 7:
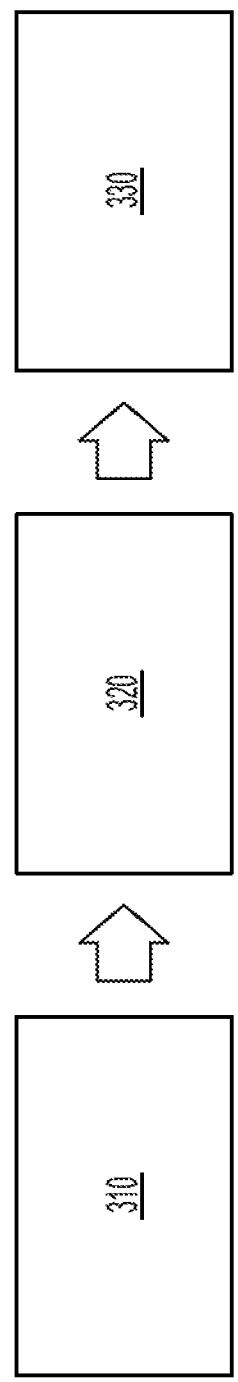
FIG. 7 is a flowchart of an example method of fabricating a wearable device having one or more integrated electronic components, in accordance with an embodiment.

FIG. 7 is a flowchart of an example method of fabricating a wearable device (e.g., wearable device 100) having one or more integrated electronic components (e.g., physiological electrodes 108A and/or 108B). At step 310, a substrate is provided, the substrate includes an elastomeric substrate, a metal oxide additive and/or a carbon source additive depending on the type of elastomer used. The elastomeric substrate is a base polymer that can include one or more of the following, for example, compounded polynorbornene, polybutadiene, ethylene propylene diene terpolymer (EPDM), natural rubber and synthetic rubber formulations, thermoplastic elastomers (TPE), thermoplastic vulcanizates (TPV), silicone rubber and its alloys. The metal oxide additive can include, for example, nickel, copper, titanium, gold, silver, palladium, chromium, phosphorus (pure metal and/or minerals and salts) and others. In example embodiments, the metal additives include plating layers of nickel, palladium, and/or gold arranged on top of copper to form a stack of two or more layers. The carbon source additive can include carbon black, carbon nanotube, graphene, and any other suitable additives and/or alternatives. The base polymer can also include dyes and pigments, titanium oxide ($TiO_2$), processing aids (oils), antioxidants, e.g., hindered amine light stabilizers (HALS) and other ultraviolet packages, or foaming agents etc. The compounded elastomeric material is mixed with one or more metal additives in a predetermined ratio. Then the mixture is cured/molded using suitable compression or injection molding technology thereby providing the substrate. In example embodiments, the base polymer is made by mixing Norsorex® material available from D-NOV GmbH of Vienna, Austria (compounded polynorbornene with processing aids and UV packages) with copper powder (99.5% purity) where the mixture comprises Norsorex® (80% by weight) and copper powder (20% by weight). In other example embodiments, the copper powder in the base polymer can be replaced with copper-chromium oxide spinel ($CuO\ Cr_2O_3$)-barium promoted in the same predetermined ratio. In example embodiments, the percent by weight of the metal additives is at least 20% and more specifically at least 30%.

In examples including copper-chromium oxide, the copper-chromium oxide absorbs laser energy (at step 320) to generate a high temperature (usually >600 degrees Celsius) on the substrate composite surface instantaneously. As a result, the elastomeric material is carbonized and the metal oxide is reduced to the elemental metal by the generated amorphous carbon at high temperature. Thus, in examples including copper-chromium oxide ($CuO\ Cr_2O_3$), a source of carbon may not be necessary. In alternate examples including other metal additives, a source of carbon is also provided at step 310.

In embodiments where the material is desired to be a foam, a foaming agent is included at step 310 and then the mixed material can be extruded pursuant to any suitable process. Similarly, in embodiments where the material is desired to be a soft material, the compounded rubber including the one or more metal additives and other miscellaneous additives can be dissolved in a suitable solvent to form a spreadable medium and the rubber can be coated on a soft material using a spreading technique or any suitable alternative.

Standard rubber compounding equipment (e.g., a two roll mill, shear blade mixer, dynamic kneader etc.) can be used with or without heat to compound the one or more metal additives and other miscellaneous additives in the base polymer. Liquid silicone rubber can be compounded using a high-speed mixer or any other standard mixing equipment. In example embodiments, a two-plate compression molder with heated platen can be used to heat soften the base polymer and compounded metal and other miscellaneous additives. The mixed materials can be cured at a temperature of 315 degrees Fahrenheit and a curing time of approximately 30 minutes in a compression-molding machine. Post curing may or may not be needed, depending on the formulation and surface finish requirements. Post curing can be done at 320 degrees Fahrenheit for 30 minutes.

The substrate can also be molded in a single-shot or multiple-shot injection molding process as per the design and application requirements. In examples, wearable device 100 includes a suitable elastomeric soft material alone. In examples, wearable device 100 includes a suitable soft elastomeric material on top of a support member made of a rigid material, for example, plastic, for stability and longevity.

At step 320, electrical circuitry is formed within the metal-filled molded elastomeric substrate. For example, the elastomeric material is activated using laser beams and metallic seeds are generated through a physical-chemical reaction. In addition to activation, the laser forms a micro-rough surface on which the metal can be firmly anchored during metallization. Laser activation can be conducted on any suitable optical fiber pulsed laser machine and laser parameters (e.g., laser scanning speed, laser power, and laser frequency) can be fine-tuned based on temperature sensitivity of the elastomeric material. In examples, the laser parameters include 0-30 W for power, 20 Hz-200 Hz for frequency, 500 mm/s-3000 mm/s for speed, SPI WF 6-WF 10, WF 16-WF 21 for waveform, and NIR (750 nm-950 nm) or IR (950 nm-11 nm) for wavelength. Any suitable laser that can provide these parameters is contemplated, for example, a NIR-Pulsed Fiber Laser, a carbon dioxide, or a redENERGY® G4 pulsed laser available from SPI Lasers UK Ltd in the United Kingdom, or any other suitable laser within the power range. In examples where the base polymer is made of 80% by weight Norsorex® and 20% by weight copper powder, the following laser parameters can be used with the redENERGY® G4 Pulsed Fiber Laser: 103 Hz for frequency, 5 W for power, 500 mm/s for mark speed and 1000 mm/s for jump speed, WF 10 for waveform, 1060 nm for wavelength.

To form the electrical circuitry, a suitable metallization process is employed after suitable pretreatment processes, including activation, etching, and cleaning etc. For example, electroplating or electroless plating can be used to form the on-part electrical circuits. In examples, the additive track build-up takes place in copper baths. In examples, the electrical circuitry is two-dimensional. In other examples, the electrical circuitry is three-dimensional and defined by the shape of the molded substrate with can include planar, curved, and interrupted (i.e., non-continuous) surfaces. Although copper can be used, it should be appreciated that other suitable metals can be used in addition to or instead of copper, for example, nickel, palladium, and gold. The plating time can range from more than 15 seconds to more than 30 minutes and the temperate can range from under 40 degrees Celsius to over 80 degrees Celsius. In examples where the base polymer is made of 80% by weight Norsorex® and 20% by weight copper powder, the following plating process can be used: industrial grade electroless copper plating for 20 minutes at 50 degrees Celsius followed by industrial grade electroless nickel plating for 20 minutes at 70 degrees Celsius.

At step 330, the on-part electrical circuits are configured to be in direct contact with the skin of an individual for good contact and connectivity. In examples, the on-part electrical circuits include one or more electrode sensors, or physiological electrode sensors (e.g., biosensors), which can be in direct contact with the skin of an individual (e.g., via dry electrode coupling).

Figure 8B:
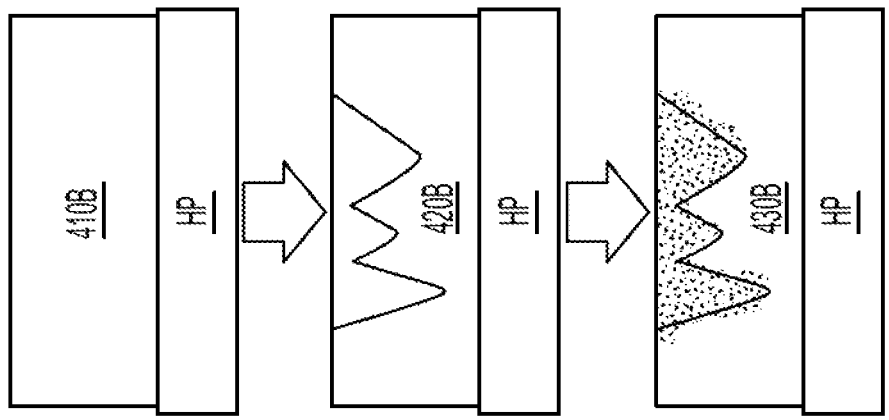
FIG. 8B shows an example method of fabricating on-part electrical circuits using a substrate having soft plastic on top of hard plastic, in accordance with an embodiment.
Figure 8A:
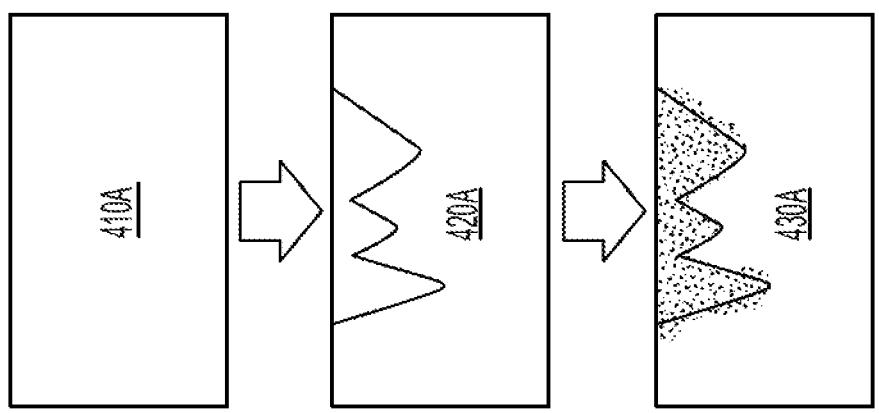
FIG. 8A shows an example method of fabricating on-part electrical circuits using a substrate having soft plastic alone, in accordance with an embodiment.

FIG. 8A shows an example method of fabricating on-part electrical circuits using a substrate having soft plastic alone. At 410A, a substrate is provided including soft material only as described herein. At 420A, one or more electrically conductive traces is structured and activated (e.g., by laser etching). At 430A, the structured and activated electrically conductive traces are plated (e.g., by electroless copper plating).

FIG. 8B shows an example method of fabricating on-part electrical circuits using a substrate having a soft plastic on top of a hard plastic HP. At 410B, a substrate is provided including a soft material on top of hard material as described herein. At 420B, one or more electrically conductive traces is structured and activated (e.g., by laser etching). At 430B, the structured and activated electrically conductive traces are plated (e.g., by electroless copper plating).

While several inventive examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive examples described herein. It is, therefore, to be understood that the foregoing examples are presented by way of example only and that, within the scope of the appended claims and equivalents thereto, inventive examples may be practiced otherwise than as specifically described and claimed. Inventive examples of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

What is claimed is:

1. A method of fabricating a wearable device having one or more integrated electronic components, comprising the steps of: providing a substrate comprising the steps of compounding an elastomeric material made of an elastomer with at least one metal oxide additive in a ratio, wherein the elastomeric material comprises a durometer equal to or less than 80 Shore A and curing or molding the compounded material to form the substrate, and wherein a percent by weight of the at least one metal oxide additive is at least 20%; forming electrical circuitry comprising at least one plating layer of the at least one metal oxide additive within the elastomeric material made of the elastomer of the substrate by structuring one or more electrically conductive traces and plating the one or more electrically conductive traces; and providing the electrical circuitry with a physiological electrode sensor, wherein the physiological electrode sensor is configured to come in direct contact with skin of an individual and apply pressure to a position on the individual.

2. The method of claim 1, wherein the step of providing the substrate further comprises providing the substrate comprising the elastomeric material made of the elastomer with a carbon source additive.

3. The method of claim 1, wherein the forming step comprises activating one or more parts of the elastomeric material made of the elastomer by laser etching to form a microrough surface within the substrate to enable the plating of the one or more electrically conductive traces.

4. The method of claim 1, wherein the plating is achieved by electroless or electrochemical plating.

5. The method of claim 1, wherein the sensor is a biosensor configured to detect one or more health parameters.

6. The method of claim 5, wherein the biosensor is coupled with the skin via dry electrode coupling.

7. The method of claim 1, further comprising the step of providing the substrate comprising the elastomeric material made of the elastomer overmolded on top of a rigid polymeric substrate.

8. The method of claim 1, wherein the step of providing the substrate further comprises providing the substrate comprising the elastomeric material made of the elastomer with a foaming agent and the method further comprises extruding the substrate to form a foam.

9. The method of claim 1, further comprising the step of coating a soft fabric with the substrate.

10. A wearable device having one or more integrated electronic components, comprising:
    a substrate comprising an elastomeric material made of an elastomer compounded with at least one metal oxide additive, wherein the elastomeric material comprises a durometer equal to or less than 80 Shore A, and wherein a percent by weight of the at least one metal oxide additive is at least 20%;
    one or more electrically conductive traces comprising at least one plating layer of the at least one metal oxide additive structured and plated within the elastomeric material made of the elastomer of the substrate; and
    a physiological electrode sensor configured to come in direct contact with skin of an individual and apply pressure to a position on the individual.

11. The wearable device of claim 10, wherein the at least one metal oxide additive includes copper-chromium oxide.

12. The wearable device of claim 10, wherein the substrate comprising the elastomeric material made of the elastomer further comprises a carbon source additive.

13. The wearable device of claim 10, wherein the physiological electrode sensor is a biosensor configured to detect one or more health parameters.

14. The wearable device of claim 13, wherein the biosensor is coupled with the skin via dry electrode coupling.

15. The wearable device of claim 10, further comprising a support member, wherein the substrate comprising the elastomeric material made of the elastomer is arranged on top of the support member.

16. The wearable device of claim 10, wherein the substrate comprising the elastomeric material made of the elastomer further includes a foaming agent.

17. The wearable device of claim 10, wherein one or more parts of the elastomeric material made of the elastomer are activated by laser etching to form a microrough surface within the substrate to enable the one or more electrically conductive traces to be plated.

18. The wearable device of claim 10, wherein the one or more electrically conductive traces are plated by electroless or electrochemical plating.

19. The wearable device of claim 10, wherein the elastomeric material made of the elastomer and the at least one metal oxide additive are mixed together at a predetermined ratio.

20. The method of claim 1, wherein the at least one plating layer is formed on top of copper to form a stack of at least two layers.

\* \* \* \* \*